United States Patent
Defossa et al.

(10) Patent No.: US 7,709,494 B2
(45) Date of Patent: May 4, 2010

(54) 4,5-DIPHENYL-PYRIMIDINYL-OXY OR -MERCAPTO SUBSTITUTED CARBOXYLIC ACIDS, METHOD FOR THE PRODUCTION AND USE THEREOF AS MEDICAMENTS

(75) Inventors: Elisabeth Defossa, Frankfurt am Main (DE); Jochen Goerlitzer, Frankfurt am Main (DE); Thomas Klabunde, Frankfurt am Main (DE); Viktoria Dietrich, Frankfurt am Main (DE); Siegfried Stengelin, Frankfurt am Main (DE); Guido Haschke, Frankfurt am Main (DE); Andreas Herling, Frankfurt am Main (DE); Stefan Bartoschek, Frankfurt am Main (DE)

(73) Assignee: Sanofi-Aventis, Frankfurt am Main (DE)

( * ) Notice: Subject to any disclaimer, the term of this patent is extended or adjusted under 35 U.S.C. 154(b) by 0 days.

(21) Appl. No.: 12/267,925

(22) Filed: Nov. 10, 2008

(65) Prior Publication Data
US 2009/0149486 A1    Jun. 11, 2009

Related U.S. Application Data

(63) Continuation of application No. PCT/EP2007/003803, filed on Apr. 30, 2007.

(30) Foreign Application Priority Data
May 11, 2006 (DE) ................ 10 2006 021 872

(51) Int. Cl.
C07D 239/34 (2006.01)
A61K 31/513 (2006.01)
(52) U.S. Cl. .................. 514/274; 544/315; 544/318
(58) Field of Classification Search ............... 544/315, 544/318; 514/274
See application file for complete search history.

(56) References Cited

U.S. PATENT DOCUMENTS
5,366,982 A    11/1994   Dereu et al.

FOREIGN PATENT DOCUMENTS
WO    WO 2004/029204    4/2004

Primary Examiner—Deepak Rao
(74) Attorney, Agent, or Firm—Jiang Lin

(57) ABSTRACT

This invention relates to a compound of formula I,

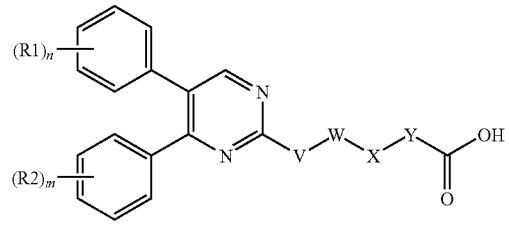

wherein R1, R2, m, n, V, W, X and Y are as defined herein, or a physiologically tolerated salt thereof, its pharmaceutical composition and use for lowering blood glucose, treating diabetes, or increasing insulin release.

16 Claims, No Drawings

4,5-DIPHENYL-PYRIMIDINYL-OXY OR -MERCAPTO SUBSTITUTED CARBOXYLIC ACIDS, METHOD FOR THE PRODUCTION AND USE THEREOF AS MEDICAMENTS

This application is a Continuation of International Application No. PCT/EP2007/003803, filed Apr. 30, 2007, which is incorporated herein by reference in its entirety.

FIELD OF THE INVENTION

The invention relates to 4,5-diphenylpyrimidinyloxy or -mercapto-substituted carboxylic acids and their physiologically tolerated salts.

BACKGROUND OF THE INVENTION

Compounds of similar structure have been described in the prior art (see WO 2004/029204).

The invention was based on the object of providing compounds which display a therapeutically utilizable effect. The object was in particular to find novel compounds suitable for the treatment of hyperglycemia and diabetes.

SUMMARY OF THE INVENTION

The invention therefore relates to compounds of the formula I,

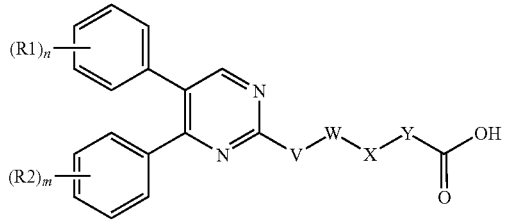

I in which the meanings are

R1, R2 independently of one another $(C_1\text{-}C_6)$-alkyl, O—$(C_1\text{-}C_6)$-alkyl, $NH_2$, $NH(C_1\text{-}C_4)$-alkyl, $N[(C_1\text{-}C_4)\text{-alkyl}]_2$, OH, CN, F, Cl, Br, O-phenyl, $CF_3$, $OCF_3$ or $OCH_3$, where alkyl may be substituted one or more times by F, Cl, Br or CN;

n 0, 1, 2, 3, 4 or 5;

m 0, 1, 2, 3, 4 or 5;

V O, S, SO or $SO_2$;

W bond, $(C_1\text{-}C_7)$-alkylene, $(C_2\text{-}C_7)$-alkenylene or $(C_2\text{-}C_7)$-alkynylene, where alkylene, alkenylene and alkynylene may be substituted one or more times by R3;

X mono-, bi- or tricyclic $(C_3\text{-}C_{12})$-cycloalkyl ring, where the cycloalkyl ring may be substituted one or more times by R4;

Y bond, $(C_1\text{-}C_4)$-alkylene, $(C_2\text{-}C_4)$-alkenylene or $(C_2\text{-}C_4)$-alkynylene, where alkylene, alkenylene and alkynylene may be substituted one or more times by R3;

R3 $NH_2$, $NH(C_1\text{-}C_4)$-alkyl, $N[(C_1\text{-}C_4)\text{-alkyl}]_2$, F, Cl, Br, CN, OH, O—$(C_1\text{-}C_6)$-alkyl, $(C_1\text{-}C_6)$-alkyl, $(C_2\text{-}C_6)$-alkenyl or $(C_2\text{-}C_6)$-alkynyl, where alkyl, alkenyl and alkynyl may be substituted one or more times by F, Cl, Br or CN;

R4 F, Cl, Br, CN, $(C_1\text{-}C_4)$-alkyl or O—$(C_1\text{-}C_4)$-alkyl, where alkyl may be substituted one or more times by F, Cl, Br or CN;

and the physiologically tolerated salts thereof.

DETAILED DESCRIPTION OF THE INVENTION

Preference is given to compounds of the formula I in which one or more radicals have the following meanings:

R1, R2 independently of one another $(C_1\text{-}C_6)$-alkyl, O—$(C_1\text{-}C_6)$-alkyl, $NH_2$, $NH(C_1\text{-}C_4)$-alkyl, $N[(C_1\text{-}C_4)\text{-alkyl}]_2$, OH, CN, F, Cl, Br, O-phenyl, $CF_3$, $OCF_3$ or $OCH_3$, where alkyl may be substituted one or more times by F, Cl, Br or CN;

n 0, 1, 2, 3, 4 or 5;

m 0, 1, 2, 3, 4 or 5;

V O, S or SO;

W bond, $(C_1\text{-}C_7)$-alkylene, $(C_2\text{-}C_7)$-alkenylene or $(C_2\text{-}C_7)$-alkynylene, where alkylene, alkenylene and alkynylene may be substituted one or more times by R3;

X mono-, bi- or tricyclic $(C_3\text{-}C_{12})$-cycloalkyl ring, where the cycloalkyl ring may be substituted one or more times by R4;

Y bond, $(C_1\text{-}C_4)$-alkylene, $(C_2\text{-}C_4)$-alkenylene or $(C_2\text{-}C_4)$-alkynylene, where alkylene, alkenylene and alkynylene may be substituted one or more times by R3;

R3 $NH_2$, $NH(C_1\text{-}C_4)$-alkyl, $N[(C_1\text{-}C_4)\text{-alkyl}]_2$, F, Cl, Br, CN, OH, O—$(C_1\text{-}C_6)$-alkyl, $(C_1\text{-}C_6)$-alkyl, $(C_2\text{-}C_6)$-alkenyl or $(C_2\text{-}C_6)$-alkynyl, where alkyl, alkenyl and alkynyl may be substituted one or more times by F, Cl, Br or CN;

R4 F, Cl, Br, CN, $(C_1\text{-}C_4)$-alkyl or O—$(C_1\text{-}C_4)$-alkyl, where alkyl may be substituted one or more times by F, Cl, Br or CN;

and the physiologically tolerated salts thereof.

Particular preference is given to compounds of the formula I in which one or more radicals have the following meanings:

R1, R2 independently of one another $(C_1\text{-}C_6)$-alkyl, O—$(C_1\text{-}C_6)$-alkyl, OH, CN, F, Cl, Br, O-phenyl, $CF_3$, $OCF_3$ or $OCH_3$;

n 0, 1, 2, 3, 4 or 5;

m 0, 1, 2, 3, 4 or 5;

V O or S;

W bond or $(C_1\text{-}C_7)$-alkylene;

X mono-, bi- or tricyclic $(C_3\text{-}C_{12})$-cycloalkyl ring, where the cycloalkyl ring may be substituted one or more times by R4;

Y bond or $(C_1\text{-}C_4)$-alkylene;

R4 F, Cl, Br, CN, $(C_1\text{-}C_4)$-alkyl or O—$(C_1\text{-}C_4)$-alkyl;

and the physiologically tolerated salts thereof.

Very particular preference is given to compounds of the formula I in which one or more radicals have the following meanings:

R1, R2 independently of one another $(C_1\text{-}C_6)$-alkyl, O—$(C_1\text{-}C_6)$-alkyl, OH, CN, F, Cl, Br, O-phenyl, $CF_3$, $OCF_3$ or $OCH_3$;

n 0;

m 0;

V O or S;

W bond or $(C_1\text{-}C_7)$-alkylene;

X mono- or bicyclic $(C_3\text{-}C_{12})$-cycloalkyl ring;

Y bond or $(C_1\text{-}C_4)$-alkylene;

and the physiologically tolerated salts thereof.

If radicals or substituents may occur more than once in the compounds of the formulae I, they may all independently of one another have the stated meaning and be identical or different.

The alkyl, alkenyl, alkynyl, alkylene, alkenylene and alkynylene radicals in the radicals W, Y R1, R2, R3 and R4 may be either straight-chain or branched.

The invention relates to compounds of the formula I in the form of their salts, racemates, racemic mixtures and pure enantiomers and diastereomers and mixtures thereof.

Physiologically tolerated salts are, because their solubility in water is greater than that of the initial or basic compounds, particularly suitable for medical applications. These salts must have a physiologically tolerated anion or cation. Suitable physiologically tolerated acid addition salts of the compounds of the invention are salts of inorganic acids such as hydrochloric acid, hydrobromic, phosphoric, metaphosphoric, nitric, sulfonic and sulfuric acids, and organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acids. The chlorine salt is particularly preferably used for medical purposes.

Suitable physiologically tolerated basic salts are ammonium salts, alkali metal salts (such as sodium and potassium salts), alkaline earth metal salts (such as magnesium and calcium salts), zinc salts, and salts of trometamol (2-amino-2-hydroxymethyl-1,3-propanediol), diethanolamine, lysine, arginine, choline, meglumine or ethylenediamine salts.

Salts with a physiologically untolerated anion or cation likewise belong within the framework of the invention as useful intermediates for preparing or purifying physiologically tolerated salts and/or for use in nontherapeutic, for example in vitro applications.

A further aspect of this invention are prodrugs of the compounds of the invention. Such prodrugs can be metabolized in vivo to a compound of the invention. These prodrugs may themselves be active or not.

The compounds of the invention may also exist in various polymorphous forms, e.g. as amorphous and crystalline polymorphous forms. All polymorphous forms of the compounds according to the invention belong within the framework of the invention and are a further aspect of the invention.

All references to "compound(s) of formula (I)" hereinafter refer to compound(s) of the formula (I) as described herein, and the salts and solvates thereof as described herein.

The compounds of the formula (I) and the physiologically tolerated salts thereof represent ideal pharmaceuticals for the treatment of elevated lipid concentrations in the blood, the metabolic syndrome, diabetes, insulin resistance, dysregulation of LDL, HDL and VLDL or cardiovascular disorders and lipid metabolism disorders, especially hyperlipidemia. The compound(s) of the formula (I) can also be administered in combination with further active ingredients.

The amount of a compound of formula (I) necessary to achieve the desired biological effect depends on a number of factors, for example the specific compound chosen, the intended use, the mode of administration and the clinical condition of the patient. The daily dose is generally in the range from 0.1 mg to 100 mg (typically from 0.1 mg to 50 mg) per day and per kilogram of body weight, for example 0.1-10 mg/kg/day. Tablets or capsules may contain, for example, from 0.01 to 100 mg, typically from 0.02 to 50 mg. For the prophylaxis or therapy of the abovementioned conditions, the compounds of formula (I) may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula (I). The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral and peroral (for example sublingual) administration, although the most suitable mode of administration depends in each individual case on the nature and severity of the condition to be treated and on the nature of the compound of formula (I) used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical preparations for oral administration may be in the form of separate units such as, for example, capsules, cachets, suckable tablets or tablets, each of which contains a defined amount of the compound of formula (I); as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula (I) with a flavoring, normally sucrose and gum arabic or tragacanth, and pastilles which comprise the compound in an inert base such as gelatin and glycerol or sucrose and gum arabic.

Combinations with Other Medicaments

The compounds of the invention can be administered alone or in combination with one or more further pharmacologically active substances which have, for example, beneficial effects on metabolic disturbances or disorders frequently associated therewith. Examples of such medicaments are 1. medicaments which lower blood glucose, antidiabetics,
2. active ingredients for the treatment of dyslipidemias,
3. antiatherosclerotic medicaments,
4. antiobesity agents,
5. antiinflammatory active ingredients
6. active ingredients for the treatment of malignant tumors
7. antithrombotic active ingredients
8. active ingredients for the treatment of high blood pressure
9. active ingredients for the treatment of heart failure and 10. active ingredients for the treatment and/or prevention of complications caused by diabetes or associated with diabetes.

They can be combined with the compounds of the invention of the formula I in particular for a synergistic improvement in the effect. Administration of the active ingredient combination can take place either by separate administration of the active ingredients to the patient or in the form of combination products in which a plurality of active ingredients are present in one pharmaceutical preparation.

Further examples of active ingredients suitable for combination products are in particular: All antidiabetics which are mentioned in the Rote Liste 2006, chapter 12; all weight-reducing agents/appetite suppressants which are mentioned in the Rote Liste 2006, chapter 1; all lipid-lowering agents which are mentioned in the Rote Liste 2006, chapter 58. They may be combined with the compound of the invention of the formula I in particular for a synergistic improvement in the effect. The active ingredient combination can be administered either by separate administration of the active ingredients to the patient or in the form of combination products in which a plurality of active ingredients is present in a pharmaceutical preparation. Most of the active ingredients mentioned hereinafter are disclosed in the USP Dictionary of USAN and International Drug Names, US Pharmacopeia, Rockville 2001.

Antidiabetics include insulin and insulin derivatives such as, for example, Lantus® (see www.lantus.com) or HMR 1964 or those described in WO2005005477 (Novo Nordisk), fast-acting insulins (see U.S. Pat. No. 6,221,633), inhalable insulins such as, for example, Exubera® or oral insulins such as, for example, IN-105 (Nobex) or Oral-Lyn™ (Generex Biotechnology), GLP-1 derivatives such as, for example, exenatide, liraglutide or those which have been disclosed in WO98/08871 or WO2005027978 of Novo Nordisk A/S, in WO01/04156 of Zealand or in WO00/34331 of Beaufour-Ipsen, pramlintide acetate (Symlin; Amylin Pharmaceuticals), and orally effective hypoglycemic active ingredients.

The orally effective hypoglycemic active ingredients include preferably
sulfonylureas,
biguanidines,
meglitinides,
oxadiazolidinediones,
thiazolidinediones,
glucosidase inhibitors,
inhibitors of glycogen phosphorylase,
glucagon antagonists,
glucokinase activators,
inhibitors of fructose-1,6-bisphosphatase,
modulators of glucose transporter 4 (GLUT4),
inhibitors of glutamine-fructose-6-phosphate amidotransferase (GFAT),
GLP-1 agonists,
potassium channel openers such as, for example, those which have been disclosed in WO 97/26265 and WO 99/03861 of Novo Nordisk A/S,
inhibitors of dipeptidylpeptidase IV (DPP-IV),
insulin sensitizers,
inhibitors of liver enzymes involved in stimulating gluconeogenesis and/or glycogenolysis,
modulators of glucose uptake, of glucose transport and of glucose reabsorption,
inhibitors of 11β-HSD1,
inhibitors of protein tyrosine phosphatase 1B (PTP1B),
modulators of the sodium-dependent glucose transporter 1 or 2 (SGLT1, SGLT2),
compounds which alter lipid metabolism such as antihyperlipidemic active ingredients and antilipidemic active ingredients,
compounds which reduce food intake,
compounds which increase thermogenesis,
PPAR and RXR modulators and
active ingredients which act on the ATP-dependent potassium channel of the beta cells.

In one embodiment of the invention, the compound of the formula I is administered in combination with an HMGCoA reductase inhibitor such as simvastatin, fluvastatin, pravastatin, lovastatin, atorvastatin, cerivastatin, rosuvastatin or L-659699.

In one embodiment of the invention, the compound of the formula I is administered in combination with a cholesterol absorption inhibitor such as, for example, ezetimibe, tiqueside, pamaqueside, FM-VP4 (sitostanol/campesterol ascorbyl phosphate; Forbes Medi-Tech, WO2005042692), MD-0727 (Microbia Inc., WO2005021497) or with compounds as described in WO2002066464 (Kotobuki Pharmaceutical Co. Ltd.), WO2005062824 (Merck & Co.) or WO2005061451 and WO2005061452 (AstraZeneca AB).

In one embodiment of the invention, the compound of the formula I is administered in combination with a PPAR gamma agonist such as, for example, rosiglitazone, pioglitazone, JTT-501, GI 262570, R-483 or CS-011 (rivoglitazone).

In one embodiment of the invention, the compound of the formula I is administered in combination with a PPAR alpha agonist such as, for example, GW9578, GW-590735, K-111, LY-674, KRP-101 or DRF-10945.

In one embodiment of the invention, the compound of the formula I is administered in combination with a mixed PPAR alpha/gamma agonist such as, for example, muraglitazar, tesaglitazar, naveglitazar, LY-510929, ONO-5129, E-3030, AVE 8042, AVE 8134, AVE 0847, or as described in PCT/US00/11833, PCT/US00/11490, DE10142734.4 or in J. P. Berger et al., TRENDS in Pharmacological Sciences 28(5), 244-251, 2005.

In one embodiment of the invention, the compound of the formula I is administered in combination with a PPAR delta agonist such as, for example, GW-501516.

In one embodiment of the invention, the compound of the formula I is administered in combination with metaglidasen or with MBX-2044 or other partial PPAR gamma agonists/antagonists.

In one embodiment of the invention, the compound of the formula I is administered in combination with a fibrate such as, for example, fenofibrate, clofibrate or bezafibrate.

In one embodiment of the invention, the compound of the formula I is administered in combination with an MTP inhibitor such as, for example, implitapide, BMS-201038, R-103757 or those described in WO2005085226.

In one embodiment of the invention, the compound of the formula I is administered in combination with a CETP inhibitor such as, for example, torcetrapib or JTT-705.

In one embodiment of the invention, the compound of the formula I is administered in combination with a bile acid absorption inhibitor (see, for example, U.S. Pat. No. 6,245,744, U.S. Pat. No. 6,221,897 or WO00/61568), such as, for example, HMR 1741 or those as described in DE 10 2005 033099.1 and DE 10 2005 033100.9.

In one embodiment of the invention, the compound of the formula I is administered in combination with a polymeric bile acid adsorbent such as, for example, cholestyramine or colesevelam.

In one embodiment of the invention, the compound of the formula I is administered in combination with an LDL receptor inducer (see U.S. Pat. No. 6,342,512), such as, for example, HMR1171, HMR1586 or those as described in WO2005097738.

In one embodiment, the compound of the formula I is administered in combination with Omacor® (omega-3 fatty acids; highly concentrated ethyl esters of eicosapentaenoic acid and of docosahexaenoic acid).

In one embodiment of the invention, the compound of the formula I is administered in combination with an ACAT inhibitor such as, for example, avasimibe.

In one embodiment of the invention, the compound of the formula I is administered in combination with an antioxidant such as, for example, OPC-14117, probucol, tocopherol, ascorbic acid, β-carotene or selenium.

In one embodiment of the invention, the compound of the formula I is administered in combination with a vitamin such as, for example, vitamin B6 or vitamin B12.

In one embodiment of the invention, the compound of the formula I is administered in combination with a lipoprotein lipase modulator such as, for example, ibrolipim (NO-1886).

In one embodiment of the invention, the compound of the formula I is administered in combination with an ATP citrate lyase inhibitor such as, for example, SB-204990.

In one embodiment of the invention, the compound of the formula I is administered in combination with a squalene synthetase inhibitor such as, for example, BMS-188494 or as described in WO2005077907.

In one embodiment of the invention, the compound of the formula I is administered in combination with a lipoprotein (a) antagonist such as, for example, gemcabene (CI-1027).

In one embodiment of the invention, the compound of the formula I is administered in combination with an HM74A receptor agonist such as, for example, nicotinic acid.

In one embodiment of the invention, the compound of the formula I is administered in combination with a lipase inhibitor such as, for example, orlistat or cetilistat (ATL-962).

In one embodiment of the invention, the compound of the formula I is administered in combination with insulin.

In one embodiment of the invention, the compound of the formula I is administered in combination with a sulfonylurea such as, for example, tolbutamide, glibenclamide, glipizide or glimepiride.

In one embodiment of the invention, the compound of the formula I is administered in combination with a biguanide such as, for example, metformin.

In another embodiment of the invention, the compound of the formula I is administered in combination with a meglitinide such as, for example, repaglinide or nateglinide.

In one embodiment of the invention, the compound of the formula I is administered in combination with a thiazolidinedione such as, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinyl-methoxy]phenyl]methyl]-2,4-thiazolidinedione.

In one embodiment of the invention, the compound of the formula I is administered in combination with an α-glucosidase inhibitor such as, for example, miglitol or acarbose.

In one embodiment of the invention, the compound of the formula I is administered in combination with an active ingredient which acts on the ATP-dependent potassium channel of the beta cells, such as, for example, tolbutamide, glibenclamide, glipizide, glimepiride or repaglinide.

In one embodiment of the invention, the compound of the formula I is administered in combination with more than one of the aforementioned compounds, e.g. in combination with a sulfonylurea and metformin, a sulfonylurea and acarbose, repaglinide and metformin, insulin and a sulfonylurea, insulin and metformin, insulin and troglitazone, insulin and lovastatin, etc.

In one embodiment of the invention, the compound of the formula I is administered in combination with an inhibitor of glycogen phosphorylase, such as, for example, PSN-357 or FR-258900 or those as described in WO2003084922, WO2004007455, WO2005073229-31 or WO2005067932.

In one embodiment of the invention, the compound of the formula I is administered in combination with glucagon receptor antagonists such as, for example, A-770077, NNC-25-2504 or as described in WO2004100875 or WO2005065680.

In one embodiment of the invention, the compound of the formula I is administered in combination with activators of glucokinase, such as, for example, RO-4389620, LY-2121260 (WO2004063179), PSN-105, PSN-110, GKA-50 or those as are described for example by Prosidion in WO2004072031, WO2004072066, WO 05103021 or WO 06016178, by Roche in WO 00058293, WO 00183465, WO 00183478, WO 00185706, WO 00185707, WO 01044216, GB 02385328, WO 02008209, WO 02014312, WO 0246173, WO 0248106, DE 10259786, WO 03095438, U.S. Pat. No. 4,067,939 or WO 04052869, by Novo Nordisk in EP 1532980, WO 03055482, WO 04002481, WO 05049019, WO 05066145 or WO 05123132, by Merck/Banyu in WO 03080585, WO03097824, WO 04081001, WO 05063738 or WO 05090332, by Eli Lilly in WO 04063194, or by Astra Zeneca in WO 01020327, WO 03000262, WO 03000267, WO 03015774, WO 04045614, WO 04046139, WO 05044801, WO 05054200, WO 05054233, WO 05056530, WO 05080359, WO 05080360 or WO 05121110.

In one embodiment of the invention, the compound of the formula I is administered in combination with an inhibitor of gluconeogenesis, such as, for example, FR-225654.

In one embodiment of the invention, the compound of the formula I is administered in combination with inhibitors of fructose-1,6-bisphosphatase (FBPase), such as, for example, CS-917.

In one embodiment of the invention, the compound of the formula I is administered in combination with modulators of glucose transporter 4 (GLUT4), such as, for example, KST-48 (D.-O. Lee et al.: Arzneim.-Forsch. Drug Res. 54 (12), 835 (2004)).

In one embodiment of the invention, the compound of the formula I is administered in combination with inhibitors of glutamine-fructose-6-phosphate amidotransferase (GFAT), as are described for example in WO2004101528.

In one embodiment of the invention, the compound of the formula I is administered in combination with inhibitors of dipeptidylpeptidase IV (DPP-IV), such as, for example, vildagliptin (LAF-237), sitagliptin (MK-0431), saxagliptin (BMS-477118), GSK-823093, PSN-9301, SYR-322, SYR-619, TA-6666, TS-021, GRC-8200, GW-825964x or as are described in WO2003074500, WO2003106456, WO200450658, WO2005058901, WO2005012312, WO2005012308, PCT/EP2005/007821, PCT/EP2005/008005, PCT/EP2005/008002, PCT/EP2005/008004, PCT/EP2005/008283, DE 10 2005 012874.2 or DE 10 2005 012873.4.

In one embodiment of the invention, the compound of the formula I is administered in combination with inhibitors of 11-beta-hydroxysteroid dehydrogenase 1 (11β-HSD1), such as, for example, BVT-2733 or those as are described for example in WO200190090-94, WO200343999, WO2004112782, WO200344000, WO200344009, WO2004112779, WO2004113310, WO2004103980, WO2004112784, WO2003065983, WO2003104207, WO2003104208, WO2004106294, WO2004011410, WO2004033427, WO2004041264, WO2004037251, WO2004056744, WO2004065351, WO2004089367, WO2004089380, WO2004089470-71, WO2004089896, WO2005016877 or WO2005097759.

In one embodiment of the invention, the compound of the formula I is administered in combination with inhibitors of protein tyrosine phosphatase 1B (PTP1B), as are described for example in WO200119830-31, WO200117516, WO2004506446, WO2005012295, PCT/EP2005/005311, PCT/EP2005/005321, PCT/EP2005/007151, PCT/EP2005/ or DE 10 2004 060542.4.

In one embodiment of the invention, the compound of the formula I is administered in combination with modulators of the sodium-dependent glucose transporter 1 or 2 (SGLT1, SGLT2), such as, for example, KGA-2727, T-1095, SGL-0010, AVE 2268 and SAR 7226 or as are described for example in WO2004007517, WO200452903, WO200452902, PCT/EP2005/005959, WO2005085237, JP2004359630 or by A. L. Handlon in Expert Opin. Ther. Patents (2005) 15(11), 1531-1540.

In one embodiment of the invention, the compound of the formula I is administered in combination with inhibitors of hormone-sensitive lipase (HSL) as described for example in WO2005073199.

In one embodiment of the invention, the compound of the formula I is administered in combination with inhibitors of acetyl-CoA carboxylase (ACC), such as, for example, those as described in WO199946262, WO200372197, WO2003072197 or WO2005044814.

In one embodiment of the invention, the compound of the formula I is administered in combination with an inhibitor of phosphoenolpyruvate carboxykinase (PEPCK), such as, for example, those as described in WO2004074288.

In one embodiment of the invention, the compound of the formula I is administered in combination with an inhibitor of glycogen synthase kinase 3 beta (GSK-3 beta), as described for example in US2005222220, WO2005085230, PCT/EP2005/005346, WO2003078403, WO2004022544, WO2003106410, WO2005058908, US2005038023, WO2005009997, US2005026984, WO2005000836, WO2004106343, EP1460075, WO2004014910, WO2003076442, WO2005087727 or WO2004046117.

In one embodiment of the invention, the compound of the formula I is administered in combination with an inhibitor of protein kinase C beta (PKC beta), such as, for example, ruboxistaurin.

In one embodiment of the invention, the compound of the formula I is administered in combination with an endothelin A receptor antagonist such as, for example, avosentan (SPP-301).

In one embodiment of the invention, the compound of the formula I is administered in combination with inhibitors of "I-kappaB kinase" (IKK inhibitors), as are described for example in WO2001000610, WO2001030774, WO2004022553 or WO2005097129.

In one embodiment of the invention, the compound of the formula I is administered in combination with modulators of the glucocorticoid receptor, like those described for example in WO2005090336.

In a further embodiment of the invention, the compound of the formula I is administered in combination with CART modulators (see "Cocaine-amphetamine-regulated transcript influences energy metabolism, anxiety and gastric emptying in mice" Asakawa, A. et al.: Hormone and Metabolic Research (2001), 33(9), 554-558);

NPY antagonists such as, for example, naphthalene-1-sulfonic acid {4-[(4-aminoquinazolin-2-ylamino)methyl] cyclohexylmethyl}amide hydrochloride (CGP 71683A);

peptide YY 3-36 (PYY3-36) or analogous compounds, such as, for example, CJC-1682 (PYY3-36 conjugated with human serum albumin via Cys34), CJC-1643 (derivative of PYY3-36 which conjugates in vivo to serum albumin) or those as are described in WO2005080424;

cannabinoid receptor 1 antagonists such as, for example, rimonabant, SR147778 or those as are described for example in EP 0656354, WO 00/15609, WO02/076949, WO2005080345, WO2005080328, WO2005080343, WO2005075450, WO2005080357, WO200170700, WO2003026647-48, WO200302776, WO2003040107, WO2003007887, WO2003027069, U.S. Pat. No. 6,509,367, WO200132663, WO2003086288, WO2003087037, WO2004048317, WO2004058145, WO2003084930, WO2003084943, WO2004058744, WO2004013120, WO2004029204, WO2004035566, WO2004058249, WO2004058255, WO2004058727, WO2004069838, US20040214837, US20040214855, US20040214856, WO2004096209, WO2004096763, WO2004096794, WO2005000809, WO2004099157, US20040266845, WO2004110453, WO2004108728, WO2004000817, WO2005000820, US20050009870, WO200500974, WO2004111033-34, WO200411038-39, WO2005016286, WO2005007111, WO2005007628, US20050054679, WO2005027837, WO2005028456, WO2005063761-62, WO2005061509 or WO2005077897;

MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]amide; (WO 01/91752)) or LB53280, LB53279, LB53278 or THIQ, MB243, RY764, CHIR-785, PT-141 or those that are described in WO2005060985, WO2005009950, WO2004087159, WO2004078717, WO2004078716, WO2004024720, US20050124652, WO2005051391, WO2004112793, WOUS20050222014, US20050176728, US20050164914, US20050124636, US20050130988, US20040167201, WO2004005324, WO2004037797, WO2005042516, WO2005040109, WO2005030797, US20040224901, WO200501921, WO200509184, WO2005000339, EP1460069, WO2005047253, WO2005047251, EP1538159, WO2004072076 or WO2004072077;

orexin receptor antagonists (e.g. 1-(2-methylbenzoxazol-6-yl)-3-[1,5]naphthyridin-4-ylurea hydrochloride (SB-334867-A) or those as are described for example in WO200196302, WO200185693, WO2004085403 or WO2005075458);

histamine H3 receptor agonists (e.g. 3-cyclohexyl-1-(4,4-dimethyl-1,4,6,7-tetrahydroimidazo[4,5-c]pyridin-5-yl) propan-1-one oxalic acid salt (WO 00/63208) or those as are described in WO200064884, WO2005082893);

CRF antagonists (e.g. [2-methyl-9-(2,4,6-trimethylphenyl)-9H-1,3,9-triazafluoren-4-yl]dipropylamine (WO 00/66585));

CRF BP antagonists (e.g. urocortin);

urocortin agonists;

β3 agonists (such as, for example, 1-(4-chloro-3-methanesulfonylmethylphenyl)-2-[2-(2,3-dimethyl-1H-indol-6-yloxy)ethylamino]ethanol hydrochloride (WO 01/83451));

MSH (melanocyte-stimulating hormone) agonists;

MCH (melanin-concentrating hormone) receptor antagonists (such as, for example, NBI-845, A-761, A-665798, A-798, ATC-0175, T-226296, T-71, GW-803430 or compounds such as are described in WO2003/15769, WO2005085200, WO2005019240, WO2004011438, WO2004012648, WO2003015769, WO2004072025, WO2005070898, WO2005070925, WO2004039780, WO2003033476, WO2002006245, WO2002002744, WO2003004027 or FR2868780);

CCK-A agonists (such as, for example, {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525), SR-146131 (WO 0244150) or SSR-125180);

serotonin reuptake inhibitors (e.g. dexfenfluramine);

mixed serotoninergic and noradrenergic compounds (e.g. WO 00/71549);

5-HT receptor agonists, e.g. 1-(3-ethylbenzofuran-7-yl)piperazine oxalic acid salt (WO 01/09111);

5-HT2C receptor agonists (such as, for example, APD-356, BVT-933 or those as are described in WO200077010, WO20077001-02, WO2005019180, WO2003064423, WO200242304 or WO2005082859);

5-HT6 receptor antagonists as are described for example in WO2005058858;

bombesin receptor agonists (BRS-3 agonists);

galanin receptor antagonists;

growth hormone (e.g. human growth hormone or AOD-9604);

growth hormone-releasing compounds (tertiary butyl 6-benzyloxy-1-(2-diisopropylaminoethylcarbamoyl)-3,4-dihydro-1H-isoquinoline-2-carboxylate (WO 01/85695));

growth hormone secretagogue receptor antagonists (ghrelin antagonists) such as, for example, A-778193 or those as are described in WO2005030734;

TRH agonists (see, for example, EP 0 462 884);

uncoupling protein 2 or 3 modulators;

leptin agonists (see, for example, Lee, Daniel W.; Leinung, Matthew C.; Rozhavskaya-Arena, Marina; Grasso, Patricia. Leptin agonists as a potential approach to the treatment of obesity.

Drugs of the Future (2001), 26(9), 873-881);

DA agonists (bromocriptine or Doprexin);

lipase/amylase inhibitors (like those described for example in WO 00/40569);

inhibitors of diacylglycerol O-acyltransferases (DGATs) as described for example in US2004/0224997, WO2004094618, WO200058491, WO2005044250, WO2005072740, JP2005206492 or WO2005013907;

inhibitors of fatty acid synthase (FAS) such as, for example, C75 or those as described in WO2004005277;

oxyntomodulin;

oleoyl-estrone or thyroid hormone receptor agonists such as, for example: KB-2115 or those as described in WO20058279, WO200172692, WO200194293, WO2003084915, WO2004018421 or WO2005092316.

In one embodiment of the invention, the further active ingredient is leptin;

see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment of the invention, the further active ingredient is dexamphetamine or amphetamine.

In one embodiment of the invention, the further active ingredient is fenfluramine or dexfenfluramine.

In another embodiment of the invention, the further active ingredient is sibutramine.

In one embodiment of the invention, the further active ingredient is mazindole or phentermine.

In one embodiment of the invention, the compound of the formula I is administered in combination with bulking agents, preferably insoluble bulking agents (see, for example, Carob/Caromax® (Zunft H J; et al., Carob pulp preparation for treatment of hypercholesterolemia, ADVANCES IN THERAPY (2001 September-October), 18(5), 230-6). Caromax is a carob-containing product from Nutrinova, Nutrition Specialties & Food Ingredients GmbH, Industriepark Höchst, 65926 Frankfurt/Main). Combination with Caromax® is possible in one preparation or by separate administration of compounds of the formula I and Caromax®. Caromax® can in this connection also be administered in the form of food products such as, for example, in bakery products or muesli bars.

It will be understood that every suitable combination of the compounds of the invention with one or more of the aforementioned compounds and optionally one or more further pharmacologically active substances will be regarded as falling within the protection conferred by the present invention.

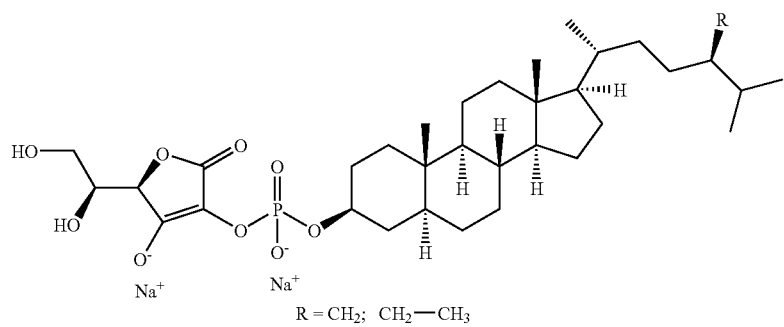

FM-VP4

-continued
JTT-501
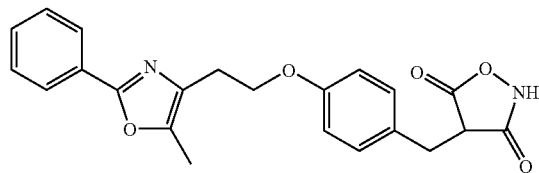
GI 262570
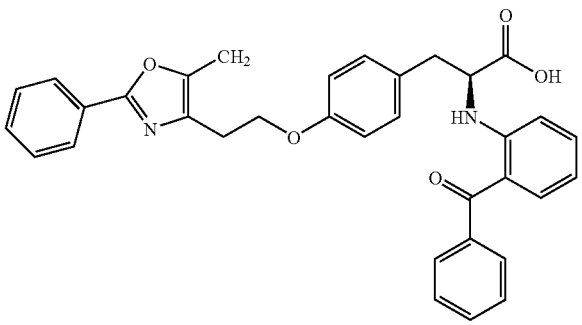
CS-011
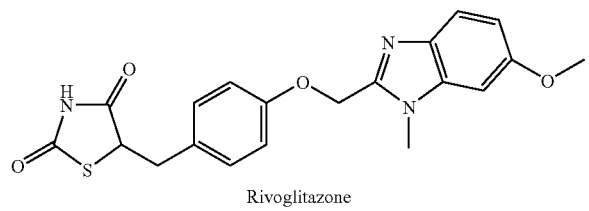
Rivoglitazone
GW-9578
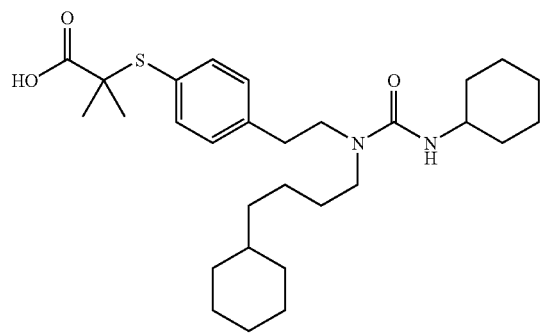
K-111
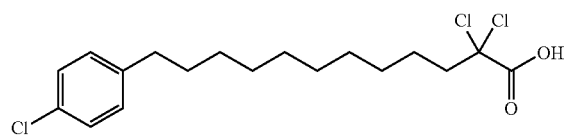
LY-674
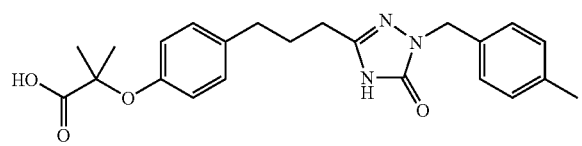
KRP-101
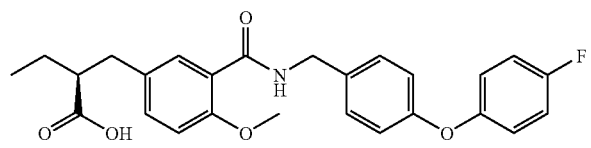
LY-510929
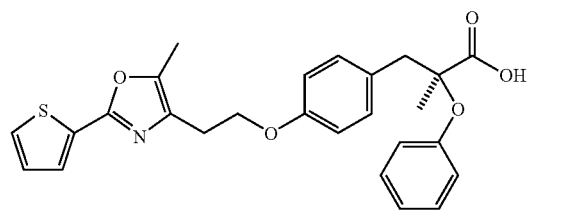
GW-501516
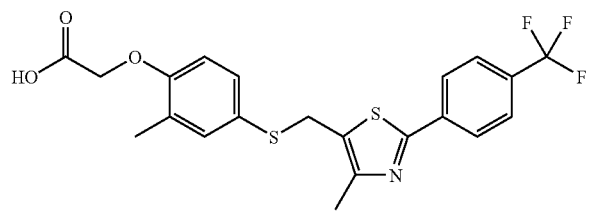
BMS-201038
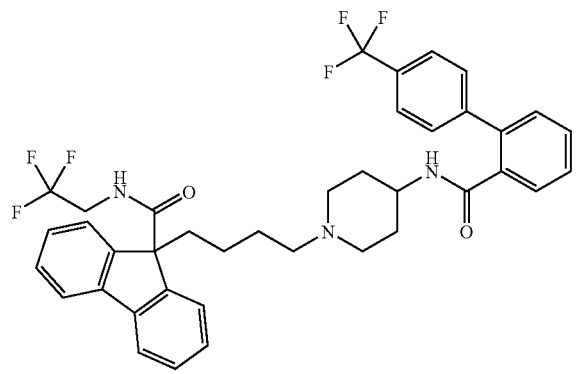

-continued
R-103757
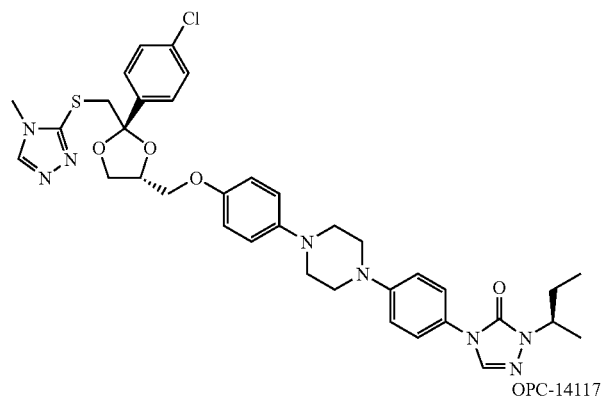
OPC-14117
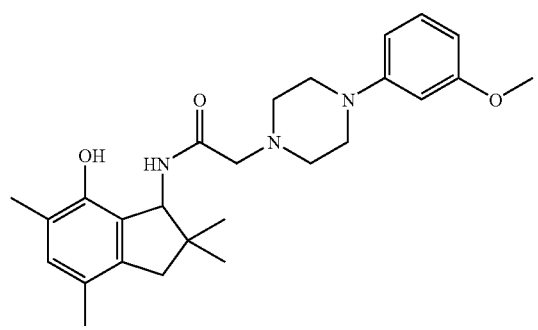
SB-204990
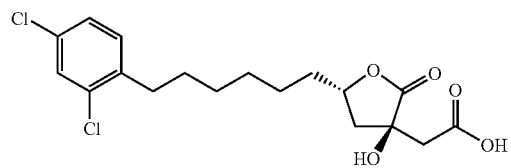
CI-1027
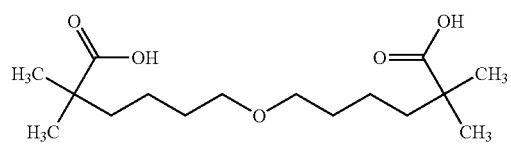
FR-258900
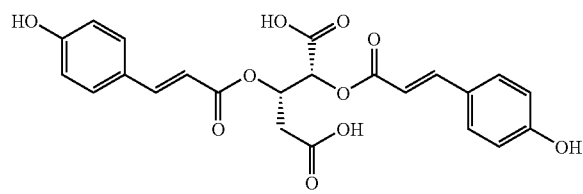
JTT-705
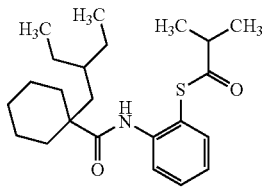
NO-1886
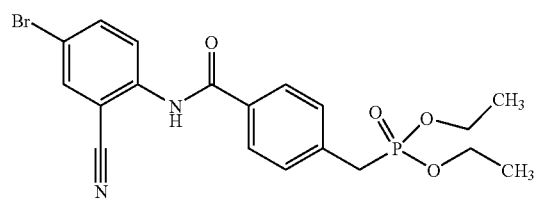
BMS-188494
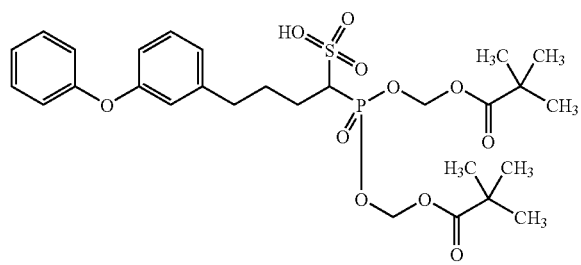
ATL-962
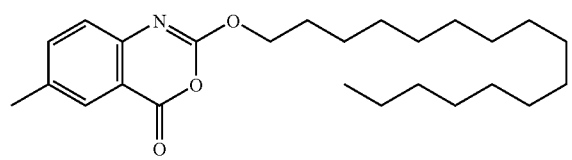
NNC-25-2504
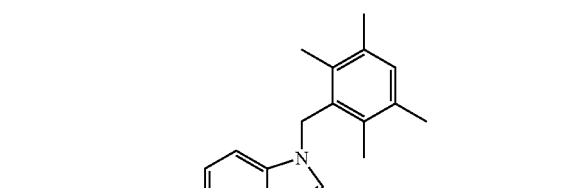
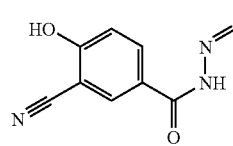

-continued
LY-2121260
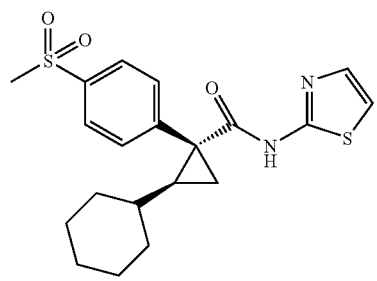
GKA-50
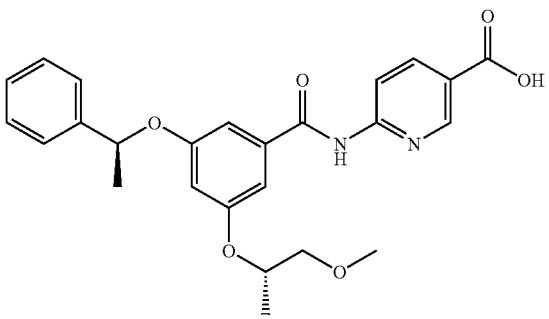
FR-225654
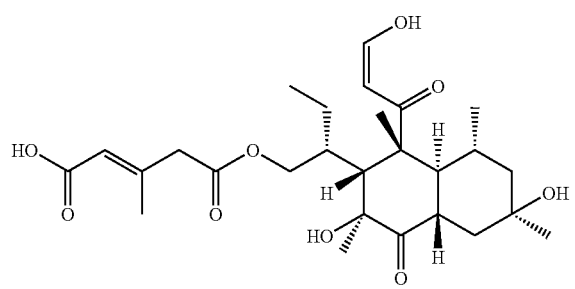
KST-48
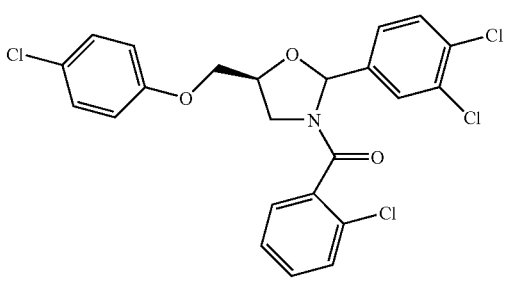
BMS-477118
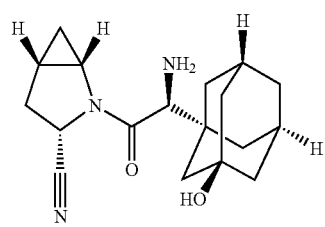
BVT-2733
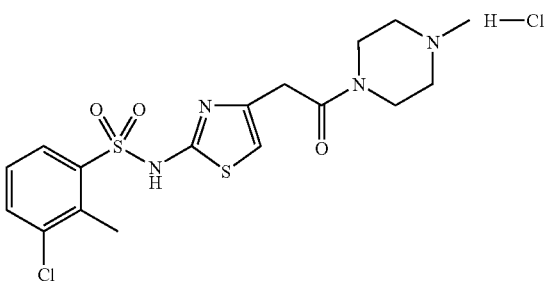
T-1095
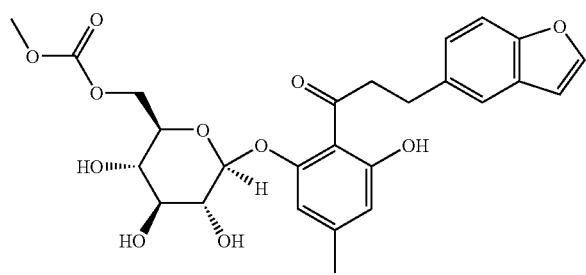
SPP-301
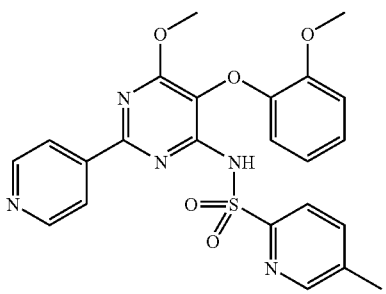

-continued
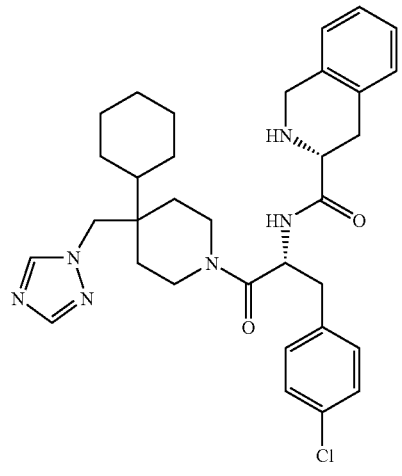
THIQ
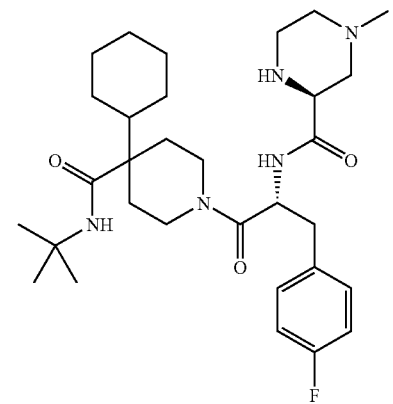
MB243
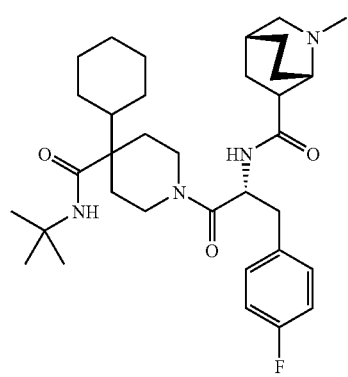
RY764
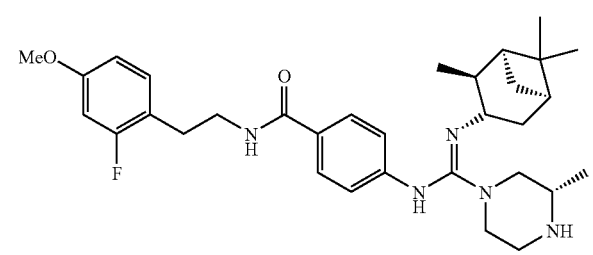
CHIR-785
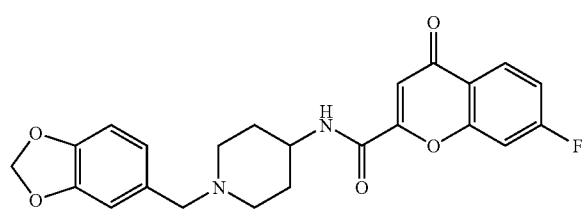
A-761
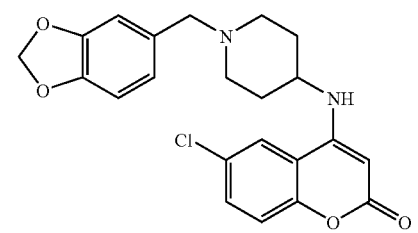
A-665798
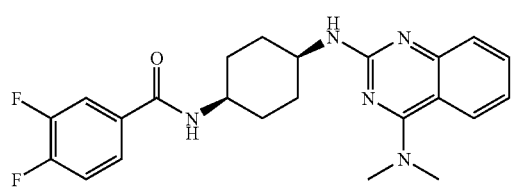
ATC-0175
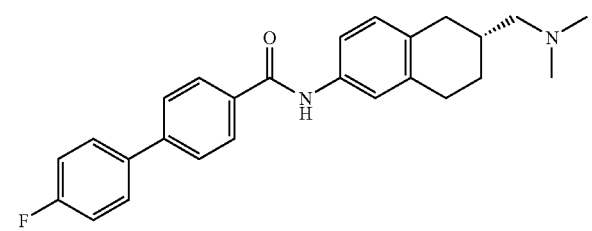
T-226296
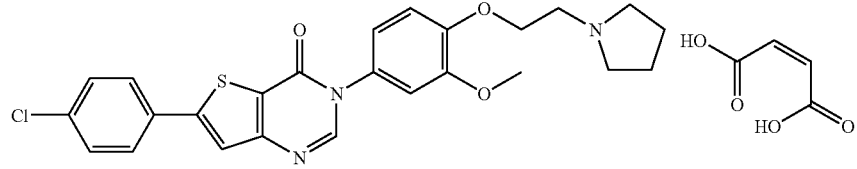
GW-803430

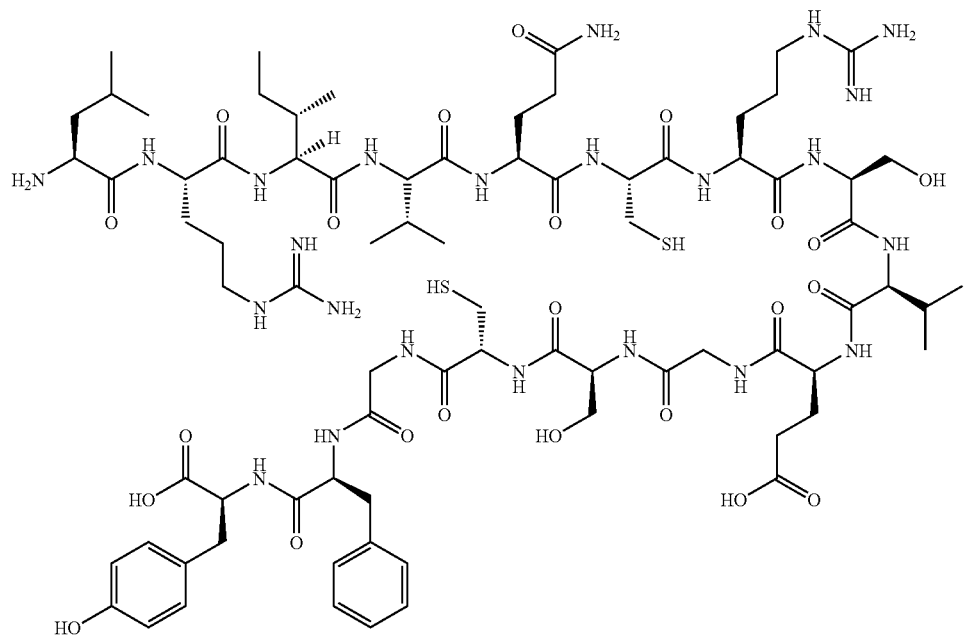
AOD-9604
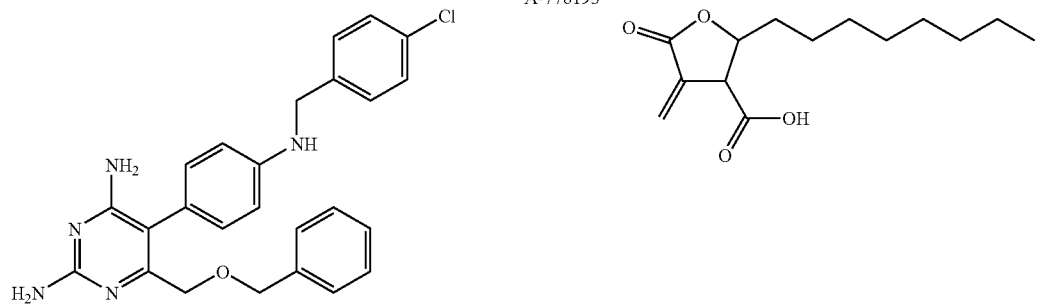
A-778193    C75
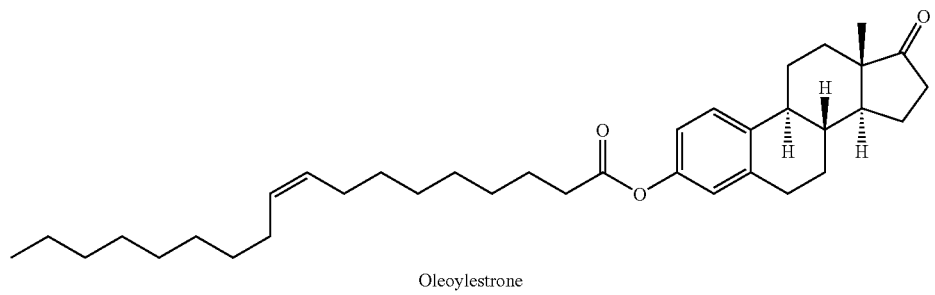
Oleoylestrone
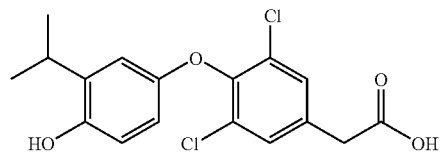
KB-2115

The invention further relates both to mixtures of stereoisomers of the formula I and to the pure stereoisomers of the formula I, and mixtures of diastereomers of the formula I and the pure diastereomers. Separation of the mixtures takes place chromatographically.

EXAMPLES

The examples detailed below serve to illustrate the invention without, however, restricting it.

TABLE 1

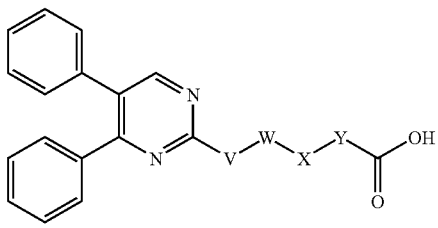

| Ex. | V | W | X | Y |
|---|---|---|---|---|
| 1 | O | —CH₂— | (1S,3R cyclohexyl di-tBu) | — |
| 2 | O | —CH₂— | (cis cyclohexyl di-tBu) | — |
| 3 | O | —CH₂— | (cis cyclopentyl di-tBu) | — |
| 4 | O | —CH₂— | (cis/trans cyclohexyl di-tBu) | — |
| 5 | S | — | (adamantyl di-tBu) | —CH₂— |
| 6 | O | — | (1S cyclohexyl di-tBu) | — |
| 7 | S | —(CH₂)₅— | (trans cyclopropyl di-tBu) | — |
| 8 | S | —(CH₂)₄— | (trans cyclopropyl di-tBu) | — |
| 9 | O | —(CH₂)₄— | (trans cyclopropyl di-tBu) | — |
| 10 | O | —CH(Et)—(CH₂)₂— | (trans cyclopropyl di-tBu) | — |

The activity of the compounds was tested as follows:

In vitro FLIPR assay with recombinant cells which express the GPCR GPR40

Function-testing assays were carried out by means of the FLIPR technique ("Fluorescence Imaging Plate Reader", Molecular Devices Corp.). For this purpose, agonist-induced changes in the intracellular concentration of $Ca^{2+}$ in recombinant HEK293 cells which expressed the GPCR. GPR40 were determined.

For the investigations, cells were seeded in 96-well microtiter plates (60 000 cells/well) and allowed to grow overnight. The medium was removed and the cells were incubated in buffer which contained the fluorescent dye fluo-4. After this loading with dye, the cells were washed, test substance was added, and changes in the intracellular $Ca^{2+}$ concentration were measured in the FLIPR instrument. Results have been presented as percentage change relative to the control (0%: no test substance added; 100%: 10 µM reference agonist linoleic acid added).

TABLE 2

| Ex. | Biological activity % activation @ 100 μM |
|---|---|
| 1 | 74 |
| 2 | 91 |
| 3 | 76 |
| 4 | 96 |
| 5 | 64 |
| 6 | 66 |
| 7 | 101 |
| 8 | 105 |
| 9 | 101 |
| 10 | 5 |

It is evident from the table that the compounds of the formula I increase the activity at the GPR40 receptor and thus are very suitable for the treatment of hyperglycemia and of diabetes. Insulin release is increased by the compounds of the formula I (see Itoh et al., Nature 422, 173-176).

The compounds of the formula I may also show a corresponding effect on the GPR120 receptor.

The compounds of the formula I can be prepared by reacting suitable starting materials of the formula II

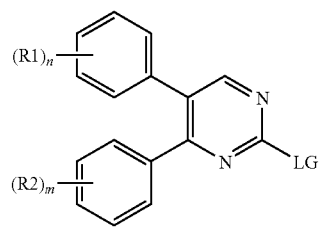

II where LG may be a leaving group such as, for example, halogen, O-mesylate, O-tosylate, O-triflate or SO$_2$Me, and n, m, R1 and R2 have the abovementioned meanings, with compounds of the formula III,

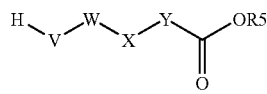

III where OR5 is a suitable protective group for ester and V is an oxygen or sulfur atom, and W, X and Y have the abovementioned meanings, under the influence of suitable inorganic and organic bases such as, for example, Na$_2$CO$_3$, Cs$_2$CO$_3$, K$_2$CO$_3$, NaH, DBU, DBN or potassium tert-butoxide in a suitable solvent such as, for example, dimethylformamide, dimethyl sulfoxide, toluene or tetrahydrofuran to give compounds of the formula IV.

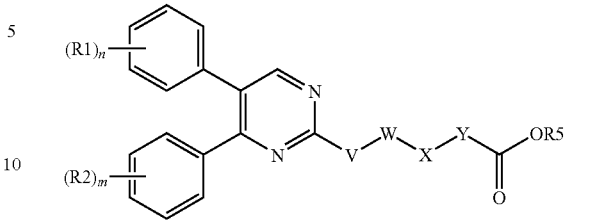

IV

Compounds of the general formula IV in which V is a sulfur atom can be oxidized by methods known from the literature to sulfoxides or sulfones.

If the ester protective group has not been eliminated under the reaction conditions, the ester protective group is subsequently eliminated by methods known from the literature to result in the compounds of the formula I.

The compounds of the formula I in which V corresponds to an oxygen atom can also be prepared by reacting suitable starting materials of the formula V (the syntheses are sufficiently well known in the literature)

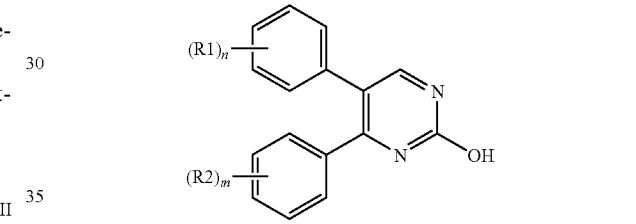

V where R1 and R2 have the abovementioned meanings, with alcohols of the general formula VI

VI under Mitsunobu conditions (O. Mitsunobu, Synthesis 1981, 1-28) to give compounds of the general formula IV in which V is an oxygen atom. By Mitsunobu conditions are meant also the use of perfluorinated triphenylphosphine and perfluoro azodicarboxylate variants which have been disclosed only in later literature (S. Dandapani, D. P. Curran, Tetrahedron 2002, 58 (20), 3855-3864). The subsequent ester cleavage to give compounds of the formula I takes place by methods known from the literature.

It is additionally possible to react compounds of the general formula II with compounds of the general formula IX

IX in the presence of suitable bases such as, for example, Na$_2$CO$_3$, Cs$_2$CO$_3$, K$_2$CO$_3$, NaH, DBU, DBN or potassium tert-butoxide in a suitable solvent such as, for example, dimethylformamide, dimethyl sulfoxide, dioxane or tetrahydrofuran to give compounds of the formula X.

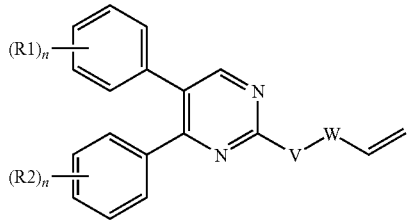

X

Compounds of the general formula X can be reacted in chlorinated solvents such as, for example, di-, tri- and tetrachloromethane in the presence of ruthenium- or molybdenum-containing metathesis catalysts with acrylic esters of the general formula XI

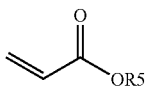

XI to give compounds of the general formula XII.

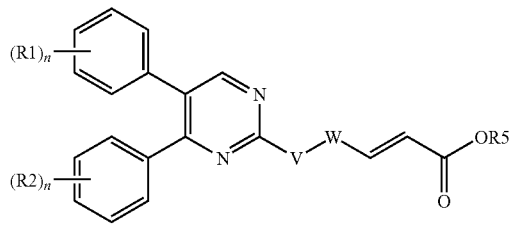

XII

The cyclopropanation of the acrylic ester can be carried out by methods known from the literature, such as, for example, with trimethylsulfoxonium iodide in dimethylsulfoxide and sodium hydride as base, to give compounds of the general formula XIII.

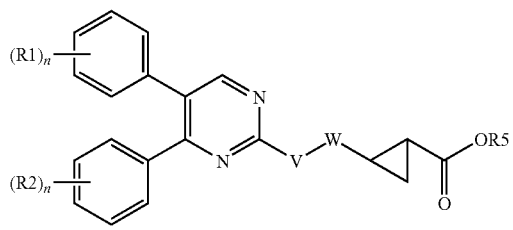

XIII

Cleavage of the respective ester by standard methods leads to compounds of the general formula XIV.

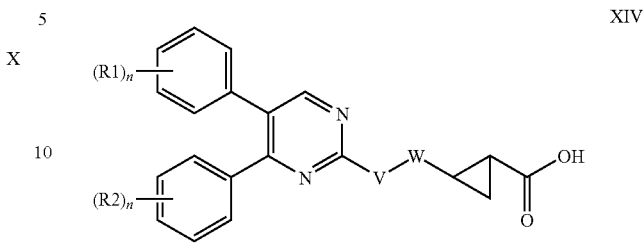

XIV

The preparation of some examples is described in detail below, and the other compounds of the formula I were obtained analogously:

Experimental Section

Example 1

(1S,3R)-3-(4,5-Diphenylpyrimidin-2-yloxymethyl)cyclohexanecarboxylic acid 94 mg (2.34 mmol) of sodium hydride (suspension in oil) were added to a solution of 178 mg (1.03 mmol) of methyl (1S,3R)-3-hydroxymethylcyclohexanecarboxylate in 5 ml of dimethylformamide at 0° C. After 30 minutes, a solution of 250 mg (0.94 mmol) of 2-chloro-4,5-diphenylpyrimidine in 2 ml of dimethylformamide was added. The reaction mixture was allowed to reach room temperature and was then heated at 60° C. for 2 hours. The solvent was concentrated under high vacuum and the residue was mixed with water and dichloromethane. After acidification with 1 N HCl, the aqueous phase was extracted with dichloromethane, dried and concentrated. The crude mixture was purified on silica gel with heptane/ethyl acetate (gradient 0% to 25% in 40 minutes, then isocratic for 20 minutes). 55 mg (15%) of the desired product were obtained.

MS: m/z=775.6 (2M−H).

Example 2 cis-(4,5-Diphenylpyrimidin-2-yloxymethyl)cyclohexanecarboxylic acid cis-(4,5-Diphenylpyrimidin-2-yloxymethyl)cyclohexanecarboxylic acid was obtained in analogy to example 1 from methyl cis-4-hydroxymethylcyclohexane-1-carboxylate and 2-chloro-4,5-diphenylpyrimidine.

MS: m/z=775.6 (2M−H).

Example 3 cis-3-(4,5-Diphenylpyrimidin-2-yloxymethyl)cyclopentanecarboxylic acid F-36009-136-A cis-3-(4,5-Diphenylpyrimidin-2-yloxymethyl)cyclopentanecarboxylic acid was obtained in analogy to example 1 from methyl cis-3-hydroxymethylcyclopentane-1-carboxylate and 2-chloro-4,5-diphenylpyrimidine.

MS: m/z=747.5 (2M−H).

Example 4

Cis/trans-4-(4,5-diphenylpyrimidin-2-yloxymethyl)cyclohexanecarboxylic cid F-36141-087-1

316 mg (2 mmol) of cis/trans-4-hydroxymethylcyclohexanecarboxylic acid were dissolved in 5 ml of dioxane, and 120 mg (3 mmol, 60%) of sodium hydride were added. After 30 minutes at room temperature, 266 mg (1 mmol) of 2-chloro-4,5-diphenylpyrimidine were added. After 48 hours at 90° C., the mixture was evaporated and taken up in ethyl acetate. The solution was washed with half-saturated sodium bicarbonate solution and saturated sodium dihydrogenphosphate solution. The organic phase was dried over sodium sulfate and concentrated. The residue was purified on silica gel with a gradient from heptane to heptane/ethyl acetate (1:1). 30 mg (8%) of the desired product were obtained.

MS: m/z=389.2 (M+H).

Example 5

[3-(4,5-Diphenylpyriidin-2-ylsulfanyl)adamantan-1-yl] acetic acid F-36141-090-1

125 mg (0.55 mmol) of (3-mercaptoadamantan-1-yl)acetic acid in 2 ml of dimethylformamide were mixed with 123 µl of DBU (0.83 mmol) and 72 mg (0.27 mmol) of 2-chloro-4,5-diphenylpyrimidine and stirred at 70° C. for 4 hours and at 90° C. for 2 hours. The mixture was purified by preparative HPLC (method A). 55 mg (45%) of the desired product were obtained.

MS: m/z=457.4 (M+H).

Example 6

(1S)-3-(4,5-Diphenylpyrimidin-2-yloxy)cyclohexanecarboxylic acid

Methyl (1S)-3-(4,5-diphenylpyrimidin-2-yloxy)cyclohexanecarboxylate 1.5 g (2.12 mmol) of diphenylperfluorodecylphosphine were added to a solution of 280 mg (1.76 mmol) of methyl (1S,3R)-3-hydroxycyclohexanecarboxylate in 2 ml of tetrahydrofuran. After 30 minutes, 525 mg (2.12 mmol) of 4,5-diphenylpyrimidin-2-ol and 2 ml of tetrahydrofuran were added, and the mixture was again stirred for 30 minutes. A solution of 1.77 g (2.12 mmol) of bis(perfluorononyl) azodicarboxylate in 2 ml of tetrahydrofuran was slowly added dropwise (exothermic reaction) and stirred at room temperature for 2 hours. It was not possible to convert the suspension into a solution by adding 1 ml of dimethylformamide. The reaction mixture was filtered with suction (precipitate corresponds to 408 mg of 4,5-diphenylpyrimidin-2-ol). The filtrate was filtered twice through a FluoroFlash cartridge and washed with methanol/water=4/1, and the filtrate was concentrated. The residue was separated on a silica gel column (heptane/ethyl acetate, 10 minutes 100% heptane, gradient from 0% to 45% ethyl acetate in 45 minutes). 28 mg (4%) of the desired product were obtained.

MS: m/z=389.1 (M+H).

(1S)-3-(4,5-Diphenylpyrimidin-2-yloxy)cyclohexanecarboxylic acid 28 mg (0.07 mmol) of methyl (1S)-3-(4,5-diphenylpyrimidin-2-yloxy)cyclohexanecarboxylate were mixed with 360 µl of tetrahydrofuran and 360 µl of 1 N aqueous lithium hydroxide solution and stirred at room temperature for 16 hours. The reaction mixture was diluted with water, acidified with sulfuric acid and extracted with ethyl acetate. The organic phase was dried with sodium sulfate and concentrated in vacuo. 17 mg (64%) of the desired product were obtained.

MS: m/z=375.5 (M+H).

Example 7

2-[5-(4,5-Diphenylpyrimidin-2-ylsulfanyl)pentyl]cyclopropanecarboxylic acid

S-6-heptenyl thioacetate 3.4 g (19.2 mmol) of 6-heptenyl-1-bromide in 15 ml of dimethylformamide were mixed with 2.4 g (21 mmol) of potassium thioacetate and stirred at room temperature for 2 hours. The mixture was taken up in 50 ml of MTBE and washed with saturated NaCl solution. Drying over sodium sulfate was followed by concentration, and the residue was employed without purification in the next stage.

2-Hept-6-enylsulfanyl-4,5-diphenylpyrimidine

The S-6-heptenyl thioacetate crude product was dissolved in 80 ml of methanol and degassed. Addition of 2.7 g (20 mmol) of potassium carbonate was followed by stirring at room temperature for 3 hours and removal of all volatile constituents in vacuo.

3.2 g (12 mmol) of 2-chloro-4,5-diphenylpyrimidine were dissolved in 45 ml of degassed dimethylformamide and added to the residue. The mixture was stirred at room temperature for 18 hours, taken up in 200 ml of MTBE and washed with saturated NaCl solution. Drying over sodium sulfate was followed by concentration and purification of the residue on silica gel with heptane/ethyl acetate (10:1). 2.9 g (67%) of the desired product were obtained.

MS: m/z=361.5 (M+H).

tert-Butyl (8-(4,5-diphenylpyrimidin-2-ylsulfanyl)oct-2-enoate 361 mg (1 mmol) of 2-hept-6-enylsulfanyl-4,5-diphenylpyrimidine and 384 mg (3 mmol) of tert-butyl acrylate in 3 ml of dichloromethane are carefully degassed, mixed with 80 mg of Grubbs II catalyst and stirred at room temperature for 18 hours. The residue after evaporation of the volatile constituents was purified on silica gel with heptane/ethyl acetate (10:1).

346 mg (75%) of the desired product were obtained.

MS: m/z=461.6 (M+H).

tert-Butyl 2-[5-(4,5-diphenylpyrimidin-2-ylsulfanyl)pentyl]cyclopropanecarboxylate 148 mg (0.675 mmol, 1.35 eq.) of trimethylsulfoxonium iodide in 3 ml of dimethyl sulfoxide were mixed with 26 mg of sodium hydride (60%) and stirred at room temperature for 1 hour. tert-Butyl (8-(4,5-diphenylpyrimidin-2-ylsulfanyl) oct-2-enoate dissolved in 1 ml of dimethyl sulfoxide were added and stirred at room temperature for 24 hours. The mixture was taken up in ethyl acetate, washed with saturated NaCl solution and dried over sodium sulfate. The residue was purified after concentration on silica gel with heptane/ethyl acetate (10:1). 96 mg (40%) of the desired product were obtained.

MS: m/z=475.7 (M+H).

2-[5-(4,5-Diphenylpyrimidin-2-ylsulfanyl)pentyl]cyclopropanecarboxylic acid 96 mg (0.2 mmol) of tert-butyl 2-[5-(4,5-diphenylpyrimidin-2-ylsulfanyl)pentyl]-cyclopropanecarboxylate were dissolved in a mixture of 2 ml of dichloromethane and 2 ml of TFA and stirred at room temperature for 2 hours. The residue after removal of all volatile constituents in vacuo was purified by preparative HPLC (method A). 60 mg (87%) of the desired product were obtained.

MS: m/z=419.14 (M+H).

Example 8

2-[5-(4,5-Diphenylpyrimidin-2-ylsulfanyl)pentyl]cyclopropanecarboxylic acid F-36341-084-1

2-[5-(4,5-Diphenylpyrimidin-2-ylsulfanyl)pentyl]cyclopropanecarboxylic acid was obtained in analogy to example 7 from 5-hexenyl-1-bromide and 2-chloro-4,5-diphenylpyrimidine.

MS: m/z=405.13 (M+H).

Example 9

2-[4-(4,5-Diphenylpyrimidin-2-yloxy)butyl]cyclopropanecarboxylic acid F-36341-088-1

2-Hex-5-enyloxy-4,5-diphenylpyrimidine 1.50 g (15 mmol) of 5-hexen-1-ol dissolved in 30 ml of dioxane were mixed with 600 mg (60%, 15 mmol) of sodium hydride and stirred at room temperature for 30 minutes. Addition of 1.7 g (7.5 mmol) of 2-chloro-4,5-diphenylpyrimidine was followed by stirring at room temperature for 6 hours. Taking up in MTBE and washing with saturated NaCl solution were followed by drying over sodium sulfate and evaporation. The residue was purified on silica gel with heptane/ethyl acetate (15:1). 1.93 g (77%) of the desired product were obtained.

MS: m/z=331.1 (M+H).

2-[4-(4,5-Diphenylpyrimidin-2-yloxy)butyl]cyclopropanecarboxylic acid was further obtained in analogy to example 7.

MS: m/z=389.1 (M+H).

Example 10

2-[3-(4,5-Diphenylpyrimidin-2-yloxy)pentyl]cyclopropanecarboxylic acid F-36341-095-1

2-[3-(4,5-Diphenylpyrimidin-2-yloxy)pentyl]cyclopropanecarboxylic acid was obtained in analogy to example 9 from 6-hepten-1-ol and 2-chloro-4,5-diphenylpyrimidine.

MS: m/z=403.6 (M+H).

Method A:
Stationary phase: Col YMC Jsphere 33×2
Gradient: (ACN+0.05% TFA):(H$_2$O+0.05% TFA) 5:95 (0 min) to 95:5 (3.4 min) to 95:5 (4.4 min)
Flow rate 1 ml/min

We claim:
1. A compound of formula I,

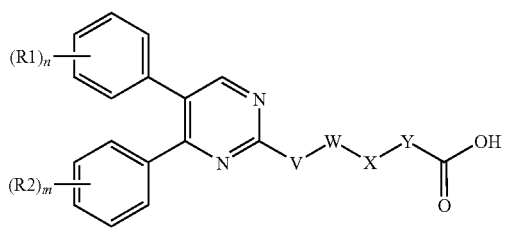

I wherein:
R1 and R2 are independently of one another (C$_1$-C$_6$)-alkyl, O—(C$_1$-C$_6$)-alkyl, NH$_2$, NH(C$_1$-C$_4$)-alkyl, N[(C$_1$-C$_4$)-alkyl]$_2$, OH, CN, F, Cl, Br, O-phenyl, CF$_3$, OCF$_3$ or OCH$_3$, wherein the alkyl moiety is optionally substituted one or more times by F, Cl, Br or CN;
n is 0, 1, 2, 3, 4 or 5;
m is 0, 1, 2, 3, 4 or 5;
V is O, S, SO or SO$_2$;
W is a bond, (C$_1$-C$_7$)-alkylene, (C$_2$-C$_7$)-alkenylene or (C$_2$-C$_7$)-alkynylene, wherein the alkylene, alkenylene and alkynylene are optionally substituted one or more times by R3;
X is mono-, bi- or tricyclic (C$_3$-C$_{12}$)-cycloalkyl ring, which is optionally substituted one or more times by R4;
Y is a bond, (C$_1$-C$_4$)-alkylene, (C$_2$-C$_4$)-alkenylene or (C$_2$-C$_4$)-alkynylene, wherein the alkylene, alkenylene and alkynylene are optionally substituted one or more times by R3;
R3 is NH$_2$, NH(C$_1$-C$_4$)-alkyl, N[(C$_1$-C$_4$)-alkyl]$_2$, F, Cl, Br, CN, OH, O—(C$_1$-C$_6$)-alkyl, (C$_1$-C$_6$)-alkyl, (C$_2$-C$_6$)-alkenyl or (C$_2$-C$_6$)-alkynyl, wherein the alkyl, alkenyl and alkynyl moieties are optionally substituted one or more times by F, Cl, Br or CN; and
R4 is F, Cl, Br, CN, (C$_1$-C$_4$)-alkyl or O—(C$_1$-C$_4$)-alkyl, wherein the alkyl moiety is optionally substituted one or more times by F, Cl, Br or CN;
or a physiologically tolerated salt thereof.

2. The compound according to claim 1, wherein:
V is O, S or SO;
or a physiologically tolerated salt thereof.

3. The compound according to claim 1, wherein:
R1 and R2 are independently of one another (C$_1$-C$_6$)-alkyl, O—(C$_1$-C$_6$)-alkyl, OH, CN, F, Cl, Br, O-phenyl, CF$_3$, OCF$_3$ or OCH$_3$;
V is O or S;
W is a bond or (C$_1$-C$_7$)-alkylene;
Y is a bond or (C$_1$-C$_4$)-alkylene; and
R4 is F, Cl, Br, CN, (C$_1$-C$_4$)-alkyl or O—(C$_1$-C$_4$)-alkyl;
or a physiologically tolerated salt thereof.

4. The compound according to claim 1, wherein:
R1 and R2 are independently of one another (C$_1$-C$_6$)-alkyl, O—(C$_1$-C$_6$)-alkyl, OH, CN, F, Cl, Br, O-phenyl, CF$_3$, OCF$_3$ or OCH$_3$;
n is 0;
m is 0;
V is O or S;
W is bond or (C$_1$-C$_7$)-alkylene;
X is mono- or bicyclic (C$_3$-C$_{12}$)-cycloalkyl ring; and
Y is bond or (C$_1$-C$_4$)-alkylene;
or a physiologically tolerated salt thereof.

5. A pharmaceutical composition comprising the compound according to claim 1 or a physiologically tolerated salt thereof, in combination with a pharmaceutically acceptable excipient.

6. A pharmaceutical composition comprising the compound according to claim 2 or a physiologically tolerated salt thereof, in combination with a pharmaceutically acceptable excipient.

7. A pharmaceutical composition comprising the compound according to claim 3 or a physiologically tolerated salt thereof, in combination with a pharmaceutically acceptable excipient.

8. A pharmaceutical composition comprising the compound according to claim 4 or a physiologically tolerated salt thereof, in combination with a pharmaceutically acceptable excipient.

9. A method for lowering blood glucose, treating diabetes, or increasing insulin release, in a patient in need thereof, comprising administering to the patient a pharmaceutically effective amount of the compound according to claim 1, or a physiologically tolerated salt thereof.

10. A method for lowering blood glucose, treating diabetes, or increasing insulin release, in a patient in need thereof, comprising administering to the patient a pharmaceutically effective amount of the compound according to claim 2, or a physiologically tolerated salt thereof.

11. A method for lowering blood glucose, treating diabetes, or increasing insulin release, in a patient in need thereof, comprising administering to the patient a pharmaceutically effective amount of the compound according to claim 3, or a physiologically tolerated salt thereof.

12. A method for lowering blood glucose, treating diabetes, or increasing insulin release, in a patient in need thereof, comprising administering to the patient a pharmaceutically effective amount of the compound according to claim 4, or a physiologically tolerated salt thereof.

13. A process for manufacturing a pharmaceutical composition comprising the compound according to claim 1 or a physiologically tolerated salt thereof, in combination with a pharmaceutically acceptable excipient, which comprises mixing the compound according to claim 1 or the physiologically tolerated salt thereof, with the pharmaceutically acceptable excipient, and converting this mixture into a form suitable for administration.

14. A process for manufacturing a pharmaceutical composition comprising the compound according to claim 2 or a physiologically tolerated salt thereof, in combination with a pharmaceutically acceptable excipient which comprises mixing the compound according to claim 2 or the physiologically tolerated salt thereof, with the pharmaceutically acceptable excipient, and converting this mixture into a form suitable for administration.

15. A process for manufacturing a pharmaceutical composition comprising the compound according to claim 3 or a physiologically tolerated salt thereof, in combination with a pharmaceutically acceptable excipient, which comprises mixing the compound according to claim 3 or the physiologically tolerated salt thereof, with the pharmaceutically acceptable excipient, and converting this mixture into a form suitable for administration.

16. A process for manufacturing a pharmaceutical composition comprising the compound according to claim 4 or a physiologically tolerated salt thereof, in combination with a pharmaceutically acceptable excipient, which comprises mixing the compound according to claim 4 or the physiologically tolerated salt thereof, with the pharmaceutically acceptable excipient, and converting this mixture into a form suitable for administration.

* * * * *